United States Patent [19]

Suzuki

[11] Patent Number: 5,002,062
[45] Date of Patent: Mar. 26, 1991

[54] AMBULATORY ELECTROCARDIOGRAPHIC APPARATUS

[75] Inventor: Takashi Suzuki, Kyoto, Japan

[73] Assignee: Sharp Kabushiki Kaisha, Osaka, Japan

[21] Appl. No.: 359,364

[22] Filed: May 31, 1989

[30] Foreign Application Priority Data

| May 31, 1988 | [JP] | Japan | 63-134801 |
| May 31, 1988 | [JP] | Japan | 63-134802 |
| May 31, 1988 | [JP] | Japan | 63-134803 |

[51] Int. Cl.⁵ .............................................. A61B 5/04
[52] U.S. Cl. ..................................... 128/696; 128/710
[58] Field of Search ............... 128/695, 696, 710, 711; 235/487, 441; 365/52

[56] References Cited

U.S. PATENT DOCUMENTS

| 4,624,263 | 11/1986 | Slavin | 128/710 |
| 4,633,881 | 1/1987 | Moore et al. | 128/710 |
| 4,715,385 | 12/1987 | Cudahy et al. | 128/710 |
| 4,843,223 | 6/1989 | Shino | 235/487 |

FOREIGN PATENT DOCUMENTS

| 0244800 | 11/1987 | European Pat. Off. | |
| 8700027 | 1/1987 | Japan | 128/637 |
| 62-267814 | 11/1987 | Japan | 235/487 |
| 62-270094 | 11/1987 | Japan | 235/487 |
| 2157463A | 10/1985 | United Kingdom | |
| WO8706447 | 1/1987 | World Int. Prop. O. | |

*Primary Examiner*—Francis Jaworski
*Assistant Examiner*—George Manuel

[57] ABSTRACT

An ambulatory electrocardiographic apparatus includes a main body which has a card mounting section for an IC memory card. The IC memory card can be inserted into the card mounting section and can be removed from the card mounting section. The IC memory card contains medical information relating to analyzing and detecting electrocardiographic signals related to the kind and condition of a disease of a patient who is being examined. The ambulatory electrocardiograph apparatus also has a control device and a display for providing a display of the signals from the IC memory card.

7 Claims, 3 Drawing Sheets

AMBULATORY ELECTROCARDIOGRAPHIC APPARATUS

BACKGROUND OF THE INVENTION

1. Field of the Invention

This invention relates to an ambulatory electrocardiographic apparatus which can detect the electrocardiographic signals from a subject. The signals can be recorded and analyzed without any restraint on the subject for a long period of time. More particularly, the invention relates to an ambulatory electrocardiographic apparatus which is provided with an IC memory card detachable from the main body of the apparatus. With the invention the electrocardiographic signals detected can be analyzed in accordance with a program stored in the IC memory card; the results of the analysis, together with the electrocardiographic signals, can be stored in the IC memory card; and these data can be dispensed on a display means of the main body of the apparatus.

2. Description of the Prior Art

In conventional ambulatory electrocardiographic apparatuses, the electrocardiographic signals detected and the results of the analysis thereof are first stored in a storage medium such as a magnetic tape mounted on the main body of the apparatus. When the recording is complete, the storage medium is dismounted from the main body and then set on an analyzing unit which is provided separately from the main body. The data stored in the storage medium is analyzed in accordance with a program for analysis stored in the analyzing unit. The results of the analysis are given on a CRT display unit or a printer connected to the analyzing unit.

In the Japanese Laid-Open Patent Publications No. 49-20981, No. 49-27087, and No. 51-90784, there are disclosed compact, light-weight ambulatory electrocardiographic apparatuses in which recording and replaying of electrocardiographic signals are performed in the same mechanism by the use of a magnetic tape as the storage medium. Japanese Laid-Open Patent Publication No. 58-19229 discloses an ambulatory electrocardiographic apparatus which is capable of recording for a long period of time by the use of a detachable magnetic bubble memory as the storage medium. In this apparatus, the electrocardiographic signals detected are compressed and stored in the bubble memory. The Japanese Laid-Open Patent Publication No. 59-222129 discloses an ambulatory electrocardiographic apparatus in which an IC memory is utilized as the storage medium. In this apparatus, different patterns of the electrocardiographic waveform detected are all marked with symbols and registered in a pattern table, so that memory capacity required for recording electrocardiographic signals for a long period of time can be considerably reduced by recording only the symbols with respect to the electrocardiographic waveform of the different patterns. Japanese Patent Application No. 63-65246 discloses an ambulatory electrocardiographic apparatus comprising a memory means, a memory control means, and a dataholding control means, wherein the electrocardiographic data are renewed and stored sequentially with time, so that only the electrocardiographic data necessary for analysis can be obtained with high efficiency and reliability.

When analyzing electrocardiographic signals, it is desirable to change the methods for analyzing and recording the electrocardiographic signals depending upon the kind of disease, the condition of the disease, the difference in medical treatment, and other conditions. However, such an elaborate analysis with the above-mentioned conventional recording and analyzing system requires a change in the program stored in the analyzing unit every time the analyzing and recording methods are changed. For this reason, not only are the number of ambulatory electrocardiographic apparatuses greatly restricted by the number and processing capability of analyzing units, but also minute analysis cannot be carried out speedily and readily. Moreover, it is desired to reduce the size and weight of electrocardiographic apparatus because these apparatuses are carried by respective subjects at all times.

SUMMARY OF THE INVENTION

The ambulatory electrocardiographic apparatus of this invention, which overcomes the above-discussed and numerous other disadvantages and deficiencies of the prior art, comprises a main body; at least one capable of storing not only various programs for analysis and recording of the electrocardiographic signals detected but also the electrocardiographic signals detected and the results of the analysis thereof. The apparatus has a card mounting section provided on the main body, into which an IC memory card can be inserted detachably from the main body. There is a control unit for making an analysis of the detected signals in accordance with a program stored in the IC memory card and for allowing the processed data to be stored in the IC memory card; and a display means for providing a display of the detected signals and the data stored in the IC memory card.

In a preferred embodiment, the ambulatory electrocardiographic apparatus also includes a transparent sheet-shaped keyboard, wherein when an IC memory card having key symbols on the surface thereof can be inserted into the card mounting section. The transparent sheet-shaped keyboard is arranged opposite to the key symbols of the IC memory card.

In a preferred embodiment, the ambulatory electrocardiographic further comprises a key panel for making a key entry associated with the IC memory card and a key panel mounting section which is provided on the main body of the apparatus and allows the key panel to be mounted detachably.

In a preferred embodiment, the IC memory card comprises at least one ROM for storing various programs for analysis and recording, and at least one RAM for storing the electrocardiographic signals detected and the results of the analysis thereof.

In a preferred embodiment, the IC memory card comprises at least one RAM for storing not only various programs for analysis and recording but also the electrocardiographic signals detected and the results of the analysis thereof and the programs can be rewritten with the use of an external system comprising an IC memory card reader/writer and a personal computer.

In a preferred embodiment, the control unit comprises a central processing unit.

In a preferred embodiment, the display means comprises a liquid crystal display device.

The objects of the invention are:

providing an ambulatory electrocardiographic apparatus in which the electrocardiographic signals detected can be treated with a desired program for analysis in the main body of the apparatus simply by inserting an appropriate IC memory card into a card mounting section of the main body, the IC memory card storing the desired program and being selected from various IC memory cards which have stored different programs for analysis, and the results of the analysis can be immediately given on a display means of the main body;

providing an ambulatory electrocardiographic apparatus in which appropriate analysis of electrocardiogram suited for the purpose can be obtained by selecting an appropriate IC memory card for each subject, and the electrocardiogram can be immediately given on a display means of the main body at the end of a recording period, thereby attaining speedy diagnosis;

providing an ambulatory electrocardiographic apparatus of small size and light weight in which the desired information such as electrocardiographic waveform, results of analysis, and the like can be given on a display means of the main body by inserting an IC memory card into a card mounting section of the main body, the IC memory card having key symbols provided on the surface thereof and storing a desired program for analysis, and by pressing the portion of a transparent sheet-shaped keyboard of the main body corresponding to the desired key symbol; and providing an ambulatory electrocardiographic apparatus of small size and light weight in which an appropriate IC memory card selected from various IC memory cards which have stored different programs for analysis is inserted into the main body of the apparatus, together with a key panel for making a key entry, thereby attaining the key entry associated with the IC memory card.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Figure 1:
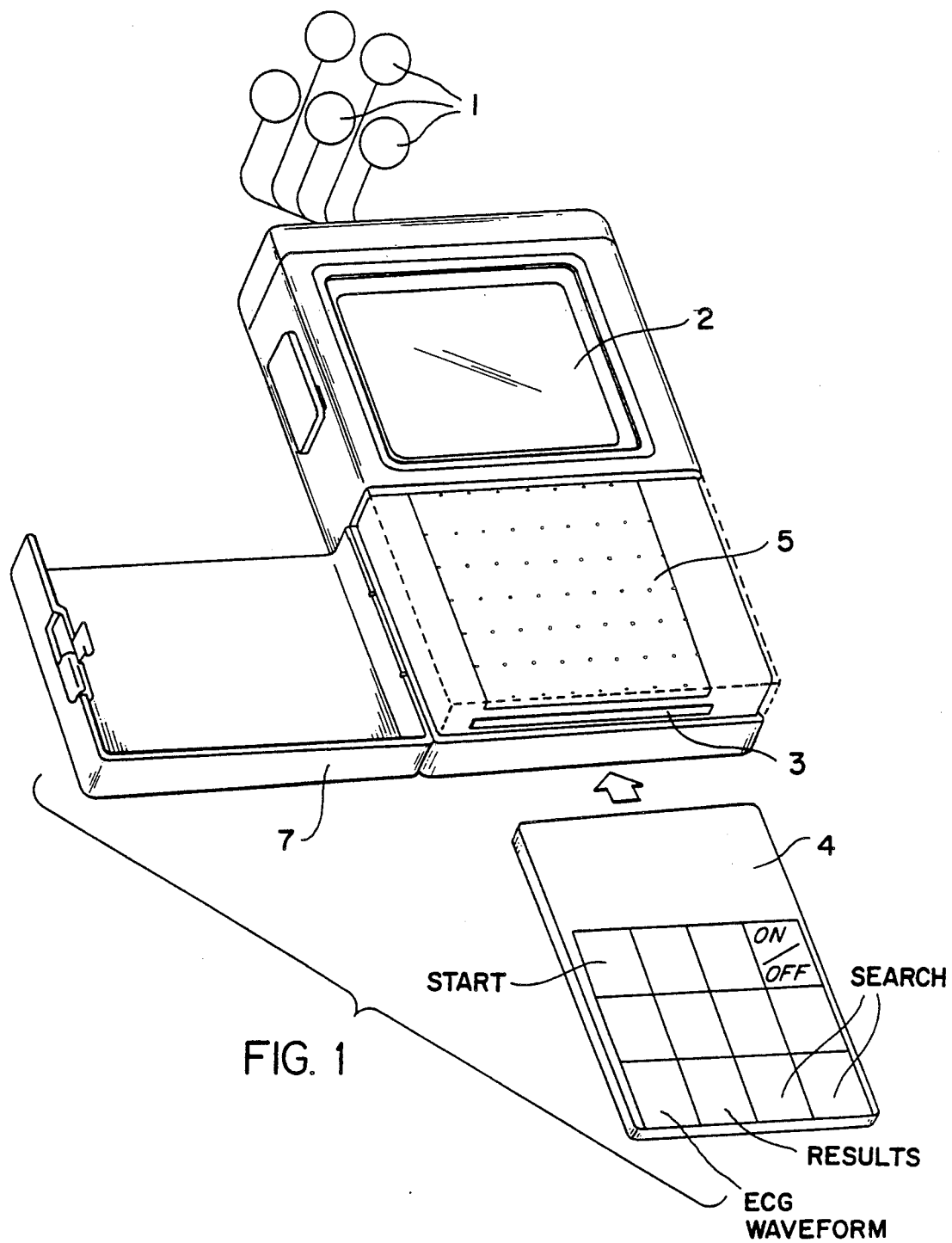
FIG. 1 is a perspective view showing an ambulatory electrocardiographic apparatus of this invention.

FIG. 1 shows an ambulatory electrocardiographic apparatus of this invention. In this figure, reference numeral 1 represents a plurality of electrodes for detecting electrocardiographic signals, reference numeral 2 is a liquid crystal display device which displays the electrocardiographic signals, the results of the analysis thereof, and other information, and reference numeral 3 is a card mounting section into which an IC memory card 4 is inserted detachably. When the IC memory card 4 is inserted in the direction indicated by the arrow in this figure, electrodes of the IC memory card 4 come in contact with electrodes provided in the inside of the card mounting section 3, so that the IC memory card 4 and the circuit in the main body of the apparatus are electrically connected with each other.

As used herein, the term "IC memory card" refers to a storage medium in the shape of a card. The IC memory card comprises a memory unit composed of read only memories (ROMs) and random access memories (RAMs), which are constituted by integrated circuits (ICs).

The IC memory card 4 can store a program for analysis depending upon the kind of disease, the condition of the disease, and the particular medical treatment. In other words, different kinds of IC memory cards can store different programs for analysis, respectively. The IC memory card 4 can further store the electrocardiographic signals detected and the results of the analysis thereof. On the surface of the IC memory card 4, there are provided key symbols.

On top of the card mounting section 3, there is disposed a transparent sheet-shaped keyboard 5. The transparent sheet-shaped keyboard 5 comprises, for example, a flexible, transparent plastic sheet having transparent electrodes arranged in X direction, and a transparent plastic substrate having transparent electrodes arranged in Y direction, both of which are formed into a laminated sheet with a plurality of small insulating buttons (shown by black dots in FIG. 1) interposed therebetween. Therefore, when the IC memory card 4 is inserted into the card mounting section 3, the key symbols on the surface of the IC memory card 4 can be seen through the transparent sheet-shaped keyboard 5, allowing a key entry by pressing the portion of the transparent sheet-shaped keyboard 5 corresponding to the desired key symbol. Although the keys of the transparent sheet-shaped keyboard 5 are defined foe each IC memory card 4 to be inserted, no elaborate explanation will be needed because the technique for changing the definition of keys is well known. The transparent sheet-shaped keyboard 5 may be of various constructions. For example, it may be composed of two transparent sheets with conductive projecting points arranged in matrix therebetween so that a contact state of the projecting point pressed with a finger can be monitored by a central processing unit (CPU) to determine which key has been pressed.

Reference numeral 7 is a cover provided rotatably on the main body, which serves to open and close the section of the card mounting section 3 and the transparent sheet-shaped keyboard 5.

Figure 2:
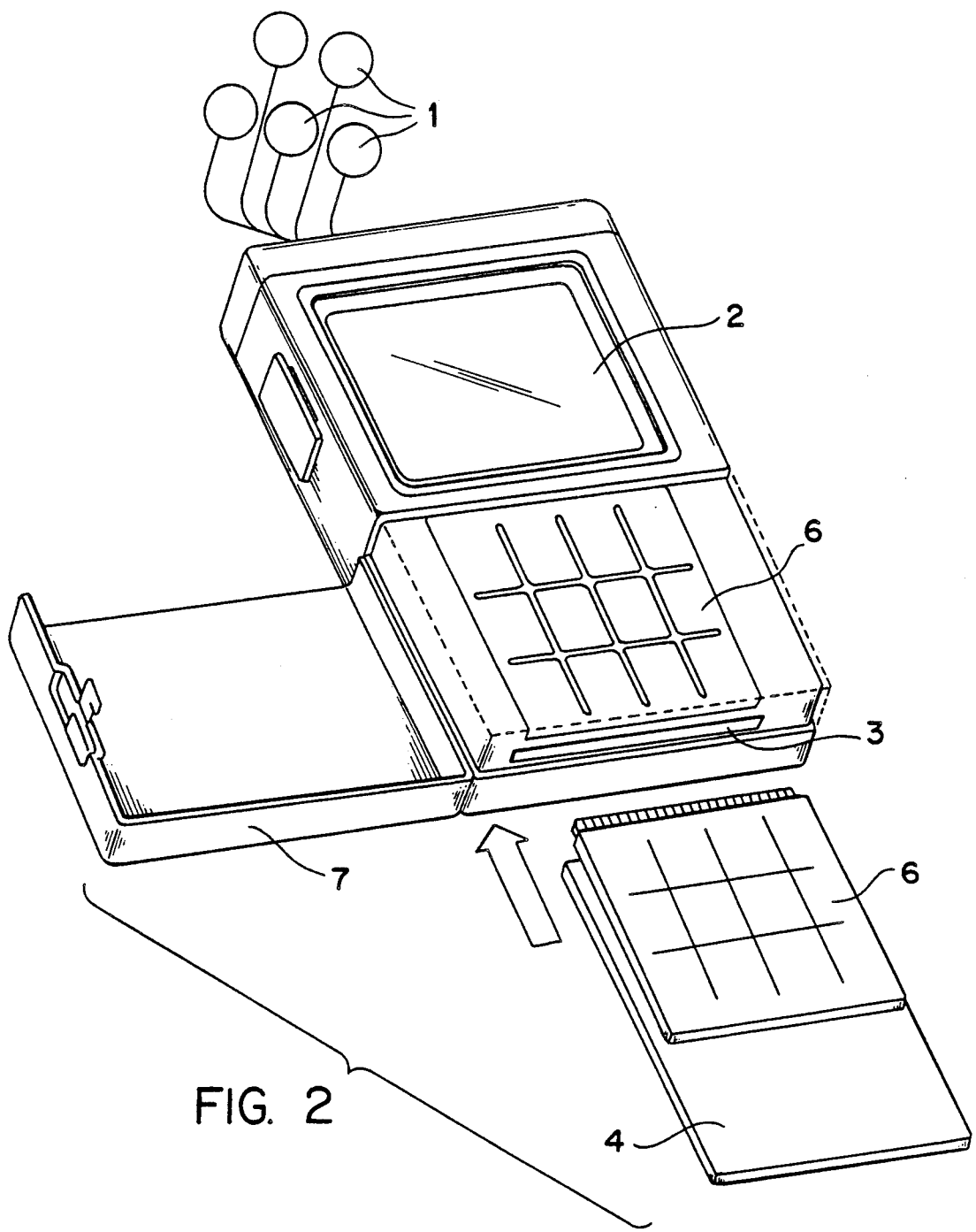
FIG. 2 is a perspective view showing another ambulatory electrocardiographic apparatus of this invention.

FIG. 2 shows another ambulatory electrocardiographic apparatus of this invention. The same parts as shown in FIG. 1 are designated by the identical reference numerals This ambulatory electrocardiographic apparatus is of the same construction as mentioned above, except that the transparent sheet-shaped keyboard 5 provided on top of the card mounting section 3 is replaced with a separate key panel 6 mountable on this section.

The key panel 6 is provided at one end with electrodes which can be connected electrically with the circuit of the main body, when the key panel 6 is inserted into the key panel mounting section, which is formed on the card mounting section 3, in the direction shown by the arrow in FIG. 2. The key panel 6 is composed of two panels, which are provided with electrodes arranged in X and Y directions, respectively, and which are attached to each other with a spacer interposed therebetween. On the surface of the key panel 6, key symbols are printed.

Figure 3:
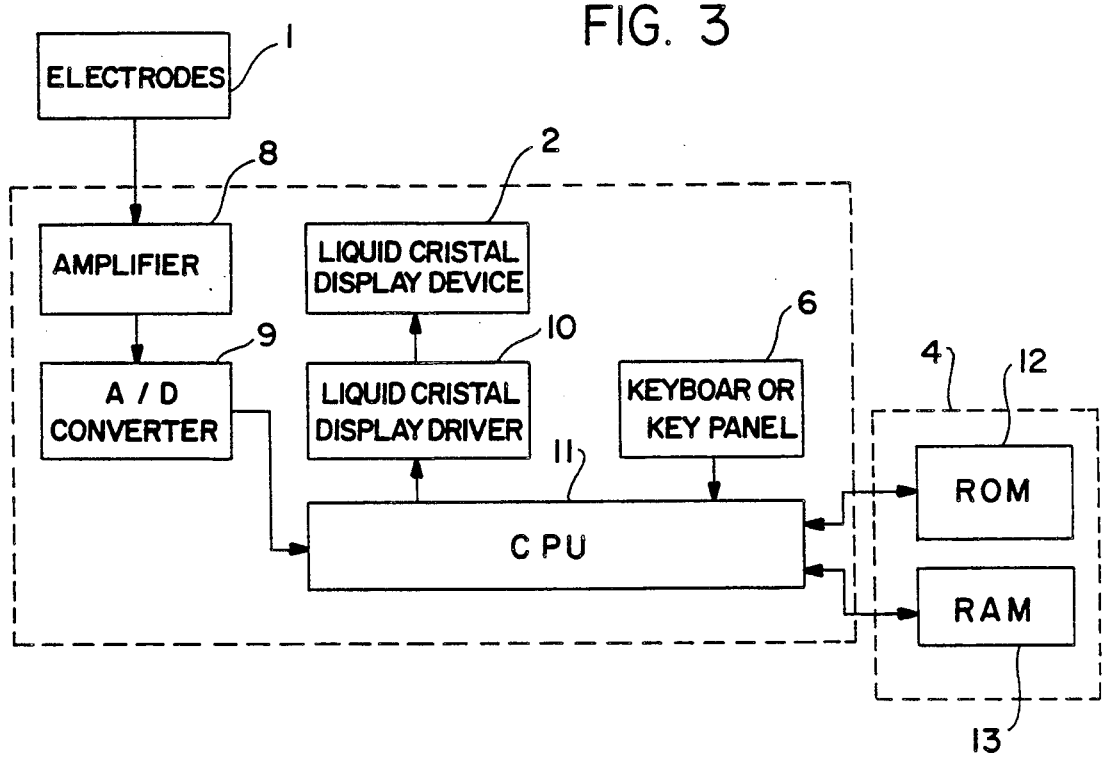
FIG. 3 is a block diagram of a circuit of the ambulatory electrocardiographic apparatus of this invention.

FIG. 3 is a block diagram of a circuit of the ambulatory electrocardiographic apparatus of this invention. (The same parts as shown in FIGS. 1 and 2 are designated by the identical reference numerals. The electrocardiographic signals detected by the electrodes 1 are amplified in an amplifier 8 and converted to the corresponding digital signals in an A/D converter 9, followed by being fed into the central processing unit (CPU) 11. The electrocardiographic digital signals fed into the CPU 11 are recorded in a RAM 13 in accordance with a program and condition statements which have been written into a ROM 12 of the IC memory card 4. An example of recording conditions is as follows: When an event entry is made by a subject through the transparent sheet-shaped keyboard 5 or the key panel 6, only the electrocardiographic waveform is recorded for a period of 15 minutes before and after the entry. Alternatively, electrocardiographic signals are analyzed in accordance with the program stored in the ROM 12, and all that is recorded is that portion of the electrocardiographic waveform which is found to be disordered. Moreover, a mode of recording can be selected to meet the particular needs such as to record the heart rate per heartbeat, in order to detect an overall change in the pattern of electrocardiographic signals throughout a period when the apparatus is attached to the body of a subject. The conditions of finding a disorder of the electrocardiographic waveform and then automatically recording its data can be set in advance by the use of the transparent sheet-shaped keyboard 5 or the key panel 6 through the interactive operation with a message given on the liquid crystal display device 2.

The electrocardiographic signals and the results of analysis recorded in the RAM 13 can be read out through the operation of the transparent sheet-shaped keyboard 5 or the key panel 6 and then given on the liquid crystal display device 2 via a liquid crystal display driver 10.

Moreover, by the use of the transparent sheet-shaped keyboard 5 or the key panel 6 through interactive operation with a message given on the liquid crystal display device 2, whether a state of attaching the electrodes 1 to the body of a subject (i.e., a state of detecting the electrocardiographic signals) and the working of the apparatus are normal or not before and during the recording of the electrocardiographic signals can be checked by determining whether the signals collected by the CPU 11 include much hum components, or by writing the signals into the RAM 13 as they are and then reading them out to determine whether they correspond to the signals which have been written the RAM 13.

Figure 4:
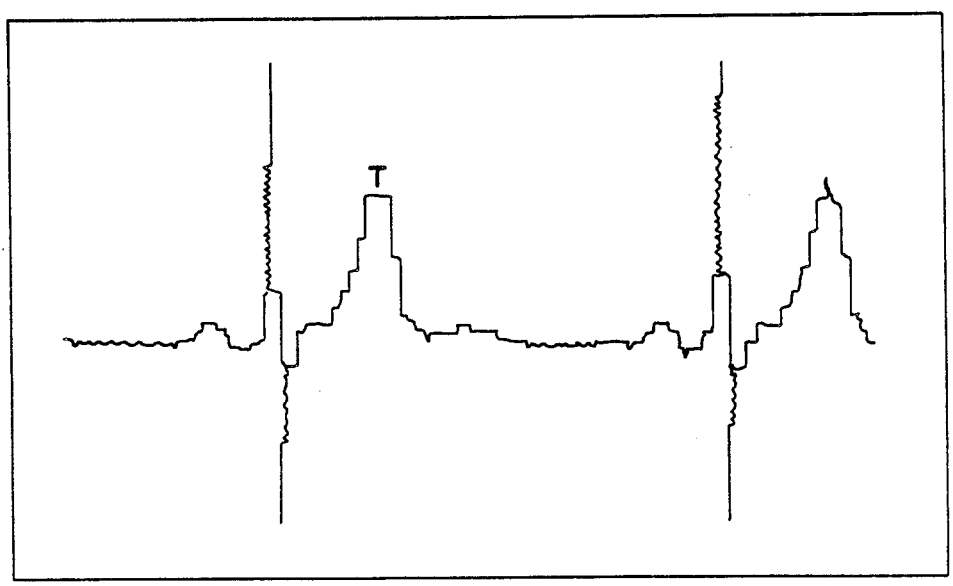
FIG. 4 shows an example of electrocardiograms given on a liquid crystal display device of the ambulatory electrocardiographic apparatus of this invention.

FIG. 4 shows an example of electrocardiograms given on the liquid crystal display device 2. In this example, a part of electrocardiographic signals recorded in the IC memory card 4 is given on the display screen of 64 dots in vertical line by 96 dots in horizontal line. With the use of such a display screen, various messages regarding the operation of the apparatus can also be given thereon.

Although in the electrocardiographic apparatus mentioned above, the programs for analysis and recording are stored in the ROM 12 and the results of the analysis are recorded in the RAM 13, the memory unit of the IC memory card 4 can also be composed only of with RAMs so that various programs are written in the RAMs with the use of an external system comprising an IC memory card reader/writer, a personal computer, etc., thereby allowing the use of many kinds of programs in a single IC memory card. With a liquid crystal television connected to the apparatus, it is also possible to provide a display of electrocardiographic waveform with high resolution.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. An ambulatory electrocardiographic apparatus operatively combined with an ICC memory card that contains medical information comprising:
   a main body;
   means operatively associated with the main body for storing a plurality of different programs for medical analysis and for recording detected electrocardiographic signals and the results of the analysis of said electrocardiographic signals;
   said main body including a card mounting section that includes means for inserting and detachably holding said IC memory card;
   said IC memory card operatively connected to said main body and including means for storing at least one program for analyzing detected electrocardiographic signals related to the kind and condition of a disease, and a particular medical treatment related to the disease;
   a control unit for making analysis of the detected signals in accordance with a program stored in said IC memory card and for making processed data to be stored in said IC memory card; and
   display means for providing a display of the detected signals and the data stored in said IC memory card.

2. An ambulatory electrocardiographic apparatus according to claim 1, further comprising a transparent sheet-shaped keyboard, wherein an IC memory card having key symbols on the surface thereof is inserted into said card mounting section, said transparent sheet-shaped keyboard is arranged next to said key symbols so that the key symbols can be seen through the transparent keyboard.

3. An ambulatory electrocardiographic apparatus according to claim 1, further comprising a key panel mounting section provided on the main body which includes means for detachably mounting a key panel;
   a key panel operatively connected to said mounting section, said key panel functioning to make a key entry.

4. An ambulatory electrocardiographic apparatus according to claim 1, wherein said IC memory card comprises at least one ROM for storing a plurality of different programs for analysis and recording, and at least one RAM for storing the electrocardiographic signals detected and the results of the analysis thereof.

5. An ambulatory electrocardiographic apparatus according claim 1, wherein said IC. memory card, comprises at least one RAM for storing a plurality of different programs for analysis and recording but also the electrocardiographic signals detected and the results of the analysis thereof and wherein said programs can be rewritten with the use of an external system comprising an IC memory card reader/writer and a personal computer.

6. An ambulatory electrocardiographic apparatus according to claim 1, wherein said control unit comprises a central processing unit.

7. An ambulatory electrocardiographic apparatus according to claim 1, wherein said display means comprises a liquid crystal display device.

* * * * *